US010271784B2

(12) United States Patent
Raymann et al.

(10) Patent No.: US 10,271,784 B2
(45) Date of Patent: Apr. 30, 2019

(54) FACILITATING RESTFUL SLEEP USING REMINDERS

(71) Applicant: Apple Inc., Cupertino, CA (US)

(72) Inventors: Roy J. Raymann, Campbell, CA (US); Wren N. Dougherty, San Francisco, CA (US); Divya Nag, Palo Alto, CA (US); Deborah M. Lambert, San Francisco, CA (US); Stephanie Greer, San Francisco, CA (US); Thomas R. Gruber, Santa Cruz, CA (US)

(73) Assignee: Apple Inc., Cupertino, CA (US)

( * ) Notice: Subject to any disclaimer, the term of this patent is extended or adjusted under 35 U.S.C. 154(b) by 603 days.

(21) Appl. No.: 14/871,875

(22) Filed: Sep. 30, 2015

(65) Prior Publication Data

US 2017/0086731 A1 Mar. 30, 2017

(51) Int. Cl.
| | |
|---|---|
| *A61B 5/00* | (2006.01) |
| *A61B 5/11* | (2006.01) |
| *A61B 5/01* | (2006.01) |
| *A61B 5/08* | (2006.01) |
| *A61B 5/024* | (2006.01) |

(Continued)

(52) U.S. Cl.
CPC .............. *A61B 5/4809* (2013.01); *A61B 5/01* (2013.01); *A61B 5/02427* (2013.01); *A61B 5/02438* (2013.01); *A61B 5/0816* (2013.01); *A61B 5/11* (2013.01); *A61B 5/6825* (2013.01); *A61B 7/003* (2013.01); *G01L 5/0038* (2013.01); *G06Q 10/109* (2013.01); *A61B 2562/0219* (2013.01); *G08B 23/00* (2013.01)

(58) Field of Classification Search
CPC .......................... A61B 5/4809; G06Q 10/109
See application file for complete search history.

(56) References Cited

U.S. PATENT DOCUMENTS

| | | | |
|---|---|---|---|
| 8,180,591 B2 | 5/2012 | Yuen et al. | |
| 2013/0135108 A1* | 5/2013 | Alameh | G06F 15/0266 340/575 |

(Continued)

FOREIGN PATENT DOCUMENTS

WO 2015/055404 4/2015

OTHER PUBLICATIONS

International Search Report dated Dec. 14, 2016 issued on corresponding PCT application No. PCT/US2016/045652.

*Primary Examiner* — Sean P Dougherty
*Assistant Examiner* — Nicholas E Kolderman
(74) *Attorney, Agent, or Firm* — Invoke

(57) ABSTRACT

In some implementations, a computing device can remind a user to perform sleep ritual activities. The computing device can automatically determine the user's sleep ritual. The users sleep ritual can include various activities performed before going to sleep. The computing device can detect when the user performs the various sleep ritual activities. The computing device can remind the user about specific sleep ritual activities when the user forgets to perform the sleep ritual activities before going to sleep. In some implementation, the computing device can perform sleep ritual activities (e.g., turning off devices, locking doors, setting the air conditioning, etc.) on behalf of the user in response to user input. In some implementation, the computing device can perform sleep ritual activities on behalf of the user automatically and without user input.

24 Claims, 8 Drawing Sheets

(51) Int. Cl.
  *A61B 7/00*   (2006.01)
  *G01L 5/00*   (2006.01)
  *G06Q 10/10*  (2012.01)
  *G08B 23/00*  (2006.01)

(56) References Cited

U.S. PATENT DOCUMENTS

| | | | |
|---|---|---|---|
| 2014/0099614 A1* | 4/2014 | Hu | G09B 19/00 |
| | | | 434/236 |
| 2014/0101611 A1 | 4/2014 | Lang et al. | |
| 2014/0125493 A1 | 5/2014 | Utter et al. | |
| 2014/0335490 A1* | 11/2014 | Baarman | A61B 5/002 |
| | | | 434/236 |
| 2015/0056589 A1 | 2/2015 | Zhang et al. | |
| 2015/0250396 A1 | 9/2015 | Ahmed et al. | |
| 2016/0007912 A1* | 1/2016 | Hu | A61B 5/002 |
| | | | 600/595 |
| 2016/0334772 A1* | 11/2016 | Nguyen | G06F 19/3481 |

* cited by examiner

FACILITATING RESTFUL SLEEP USING REMINDERS

TECHNICAL FIELD

The disclosure generally relates to detecting and identifying user activity.

BACKGROUND

Most people perform a regular or recurring, set of activities (e.g., a sleep ritual) before they go to sleep at night. This sleep ritual can include activities such as brushing teeth, taking the dog out, locking the front door, turning off appliances, setting a morning alarm, checking a calendar, and/or other activities. Sometimes a person can have difficulty falling to sleep because they fear that they have forgotten to perform one of these sleep ritual activities.

SUMMARY

In some implementations, a computing device can remind a user to perform sleep ritual activities. The computing device can automatically determine the user's sleep ritual. The users sleep ritual can include various activities performed before going to sleep. The computing device can detect when the user performs the various sleep ritual activities. The computing device can remind the user about specific sleep ritual activities when the user forgets to perform the sleep ritual activities before going to sleep. In some implementation, the computing device can perform sleep ritual activities (e.g., turning off devices, locking doors, setting, the air conditioning, etc.) on behalf of the user in response to user input. In some implementation, the computing device can perform sleep ritual activities on behalf of the user automatically and without user input.

Particular implementations provide at least the following advantages: by reminding the user to perform sleep ritual activities, the computing device can help the user get a restful night sleep the computing device can automatically adjust other devices in the user's home so that the user can get a restful sleep; and the computing device can help the user conserve energy and/or create a safe environment for sleeping.

Details of one or more implementations are set forth in the accompanying drawings and the description below. Other features, aspects, and potential advantages will be apparent from the description and drawings, and from the claims.

DESCRIPTION OF DRAWINGS

Like reference symbols in the various drawings indicate like elements.

DETAILED DESCRIPTION

Overview

Figure 1:
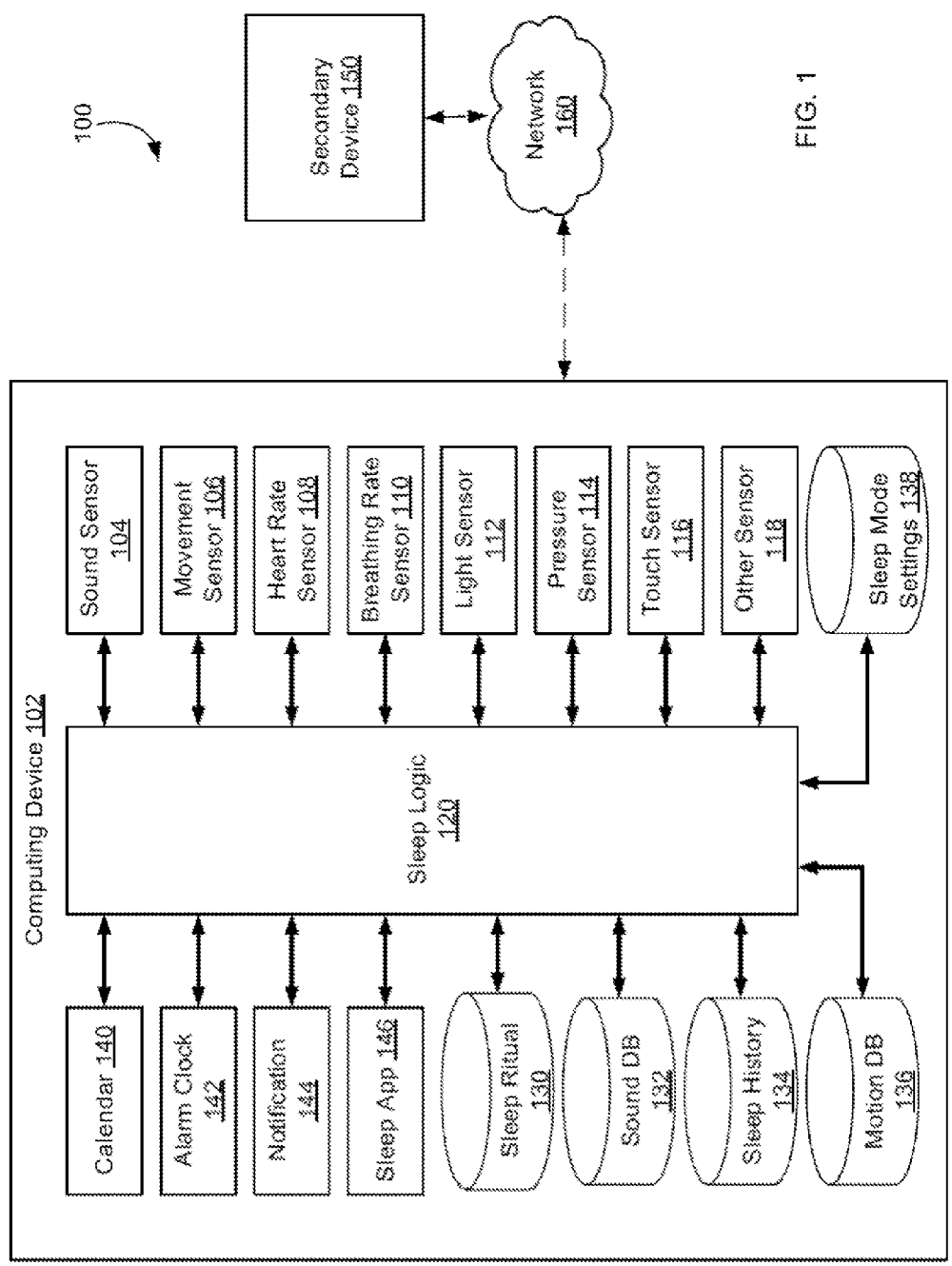
FIG. 1 is a block diagram of an example system 100 for facilitating restful sleep using reminders.

FIG. 1 is a block diagram of an example system 100 for facilitating, restful sleep using reminders. In some implementations, system 100 can include computing device 102. For example, computing device 102 can be a mobile device, such as a smartphone, tablet computer, laptop computer, etc. Computing device 102 can be a wearable device, such as a smart watch, smart eye glasses, smart contacts, etc., for example. Computing device 102 can be a personal computing device of a user. For example, computing device 102 may be a single user device.

In some implementations, computing device 102 can include sleep logic 120. For example, sleep logic 120 can be an operating system software process (e.g., function, utility, daemon, etc.). Sleep logic 120 can be an independent software process (e.g., a standalone application). Sleep logic 120 can interact with various sensors of computing device 102 to detect various signals indicating when the user intends to sleep, when the user actually falls asleep, and when the user wakes up. Sleep logic 120 can use the detected signals to determine whether the user has performed the user's sleep ritual activities. When the user has not performed one of the user's sleep ritual activities, computing device 102 can remind the user to perform the missed or skipped activity so that the user can sleep without worrying about whether the user forgot to do something before bed.

Detecting Sleep

In some implementations, computing device 102 can detect when the user falls asleep. In some implementations, sleep logic 120 can detect when the user fails asleep based on user input. For example, when the user is using computing device 102 (e.g., using an application, providing user input, etc.), then the user is performing a conscious human activity and cannot possibly be sleeping. When the user stops using computing device 102 for a period of time (e.g., 5 hours, 7 hours, etc.), then sleep logic 120 can determine that the user is asleep. Thus, if, for example, the display of computing device 102 is dark (e.g., not illuminated) for a period of 7 hours, sleep logic 120 can determine that the user was sleeping during the 7 hour period. Sleep logic 120 can determine the sleep start time based on the time when the sleep period began. For example, if the last user input before the sleep period was at 10:36 pm, then sleep logic 120 can determine that the sleep period began at 10:36 pm. If the screen went dark at 11:16 pm and stayed dark for 7.5 hours, then sleep logic 120 can determine that the sleep period began at 11:16 pm.

In some implementations, sleep logic 120 can detect when the user falls asleep based on sensor data. For example, computing device 102 can include various sensors that can detect environmental and/or biometric signals that can be used to determine when the user is sleeping. Sleep logic 120 can detect sleep based on a single signal (e.g., heartrate) or a combination of signals (e.g., heartrate, breathing, movement, etc.). For example, sleep logic 120 can use multiple signals to improve the probability that the sleep determination is correct.

In some implementations, computing device 102 can include sound sensor 104 (e.g., a microphone) that can detect sounds near computing device 102. In some implementations, sound sensor 104 can detect sleep sounds. For example, sleep logic 120 can initially determine that the user is sleeping based on the absence of user input, as described above. Sound sensor 104 can collect sleep sounds while the user is sleeping (e.g., snoring, slow breathing, bed sounds generated when the user moves in the bed, etc.). Sleep logic 120 can store the collected sleep sounds in sound database 106. When sleep logic 120 later detects similar sleep sounds, sleep logic 120 can analyze the sleep sounds and determine that the sleep sounds correspond to the user sleeping by comparing the detected sleep sounds to the sleep sounds in sound database 132.

In some implementations, computing device 102 can include movement sensor 106. For example, movement sensor 106 can be an accelerometer. Movement sensor 106 can detect when computing device 102 is moving, for example. When the user of computing device 102 is holding or wearing computing device 102 and the user moves, movement sensor 106 can detect the movement and sleep logic 120 can determine that the user is awake. When movement sensor 106 detects very little movement (e.g., below a threshold frequency, or threshold magnitude), then sleep logic 120 can determine that the user is asleep.

In some implementations, computing device 102 can include heart rate sensor 108. For example, heart rate sensor 108 can be a motion sensor. For example, the motion sensor can be worn near the heart or on the wrist to detect motion corresponding to the user's pulse. Heart rate sensor 108 can be a microphone. For example, the microphone can be worn on the wrist near the radial artery to detect sounds corresponding to the user's pulse. Heart rate sensor 108 can be a photoplethysmogram (PPG) sensor, such as a pulse oximeter, camera, or other optical sensor. Heart rate sensor 108 can optically obtain a plethysmogram by illuminating the skin and measuring changes in light absorption to detect the user's pulse. Sleep logic 120 can use the pulse data generated by heart rate sensor 108 to determine a heart rate for the user. Sleep logic 120 can use the pulse data generated by heart rate sensor 108 to determine the variability in the user's pulse. For example, pulse or heart rate variability decreases as the user transitions from a wake state to a sleep state. Sleep logic 120 can determine that the user is sleeping when the user's heart rate and/or heart rate variability is below respective threshold values. Sleep logic 120 can determine that the user is awake when the user's heart rate and/or heart rate variability are above respective threshold values.

In some implementations, computing device 102 can include breathing rate sensor 110. For example, breathing rate sensor 108 can be a microphone. For example, the microphone can detect sounds corresponding to breaths taken by the user. Breathing rate sensor 108 can be a photoplethysmogram (PPG) sensor such as a pulse oximeter, camera, or other optical sensor. Breathing rate sensor 108 can optically obtain a plethysmogmm by illuminating the skin and measuring changes in light absorption to detect when the user takes a breath. Sleep logic 120 can use the breathing rate data generated by breathing rate sensor 108 to determine a breathing rate (e.g., frequency of breaths), breathing rate variability, and/or breathing amplitude (e.g., how big or deep the breaths are) for the user. Sleep logic 120 can determine that the user is sleeping when the user's breathing rate, breathing rate variability, and/or breathing amplitude are below respective threshold values. Sleep logic 120 can determine that the user is awake when the user's breathing rate, breathing rate variability, and/or breathing, amplitude are above respective threshold values. For example, slow, regular breaths can indicate that the user is sleeping while faster, inconsistent breathing can indicate that the user is awake.

In some implementations, computing device 102 can include light sensor 112. For example, light sensor 112 can be a photoresistor that detects the light intensity of the environment around computing device 102. Sleep logic 120 can use the light intensity data generated by light sensor 112 to determine whether the user is sleeping. For example, humans usually enjoy sleeping in a dark environment. Thus, if light sensor 112 detects that the light intensity is above a threshold intensity value, computing device 102 can determine that the user is awake. If light sensor 112 detects that the light intensity is below the threshold value, computing device 102 can determine that the user is sleeping.

In some implementations, computing device 102 can include pressure sensor 114. For example, pressure sensor 114 can be incorporated into or behind a touch sensitive display of computing device 102. A user can touch and apply pressure to the touch sensitive display and pressure sensor 114 can determine the amount of pressure being applied to the touch sensitive display. To determine the start of sleep, the user can be prompted to apply and hold pressure to the touch sensitive display. When the user falls asleep, the user will not be able to continue applying pressure to the display. Sleep logic 120 can receive pressure data from pressure sensor 114, determine the amount of pressure being applied to the display by the user has decreased (e.g., below some pressure value), and determine that the user is asleep based on the decrease in pressure.

In some implementations, computing device 102 can include touch sensor 116. For example, touch sensor 116 can be a touch sensitive display, a button, or some other device that is responsive to the user's touch. Sleep logic 120 can use the touch sensor data generated by touch sensor 116 to determine if the user is awake or asleep. For example, if touch sensor 116 detects that the user has touched computing device 102 (e.g., the touch sensitive display, button, etc.), then sleep logic 120 can determine that the user is awake. If touch sensor 116 does not detect the user touching computing device 102 for a period of time (e.g., 4 hours, 6 hours, etc.), then sleep logic 120 can determine that the user is asleep.

In some implementations, computing device 102 can include other sensors 118. For example, other sensors 118 can include a temperature sensor, a location sensor, or any other sensor that can generate data that can be used to inform the sleep determination. For example, the temperature sensor can detect the heat of the user's skin. Typically, skin temperature (e.g., surface temperature) of the human body increases while sleeping. Thus, sleep logic 120 can determine that the user is sleeping when the skin temperature data generated by the temperature sensor indicates an increase in the user's body temperature above a threshold temperature. When other sensors 118 is a location sensor, for example, sleep logic 120 can determine that the user is sleeping when the location of computing device 102 is the user's home or at some other place where the user typically sleeps. For example, sleep logic 120 may determine that the user is still awake when the location of computing device 102 is the user's place of business.

In some implementations, sleep logic 120 can determine when the user is awake using the sensors described above. For example, the various sensors can detect conscious human activity and sleep logic 120 can determine that the user is awake based on the detected activity. For example, sleep logic 120 can receive sensor data that indicates conscious movement, talking, increased heart rate, increased breathing rate, increased lighting, and/or use of computing device 102 (e.g., touch input) and determine that the user is awake based on the sensor data. Sleep logic 120 can determine the wake time based on when the first sensor detected conscious human activity. For example, the wake time can correspond to the time when a sensor first detected conscious movement, talking, increased heart rate, increased breathing rate, increased lighting, and/or use of computing device 102 (e.g., touch input).

In some implementations, the sleep start time and sleep end time (wake time) can be used to determine the sleep period. For example, if the sleep start time is 11 pm and the sleep end time is 6 am, then the sleep period (duration) is 7 hours (e.g., 6 am-11 pm=7 hours). In some implementations, sleep logic 120 can store sleep the sleep start time, sleep end time, and/or sleep duration in sleep history database 134. For example, each record in sleep history database 134 can include sleep data for an instance of sleep. The sleep data can include sleep start time, sleep end time, sleep duration, and sensor data collected while the user is sleeping, as described above. The sensor data can be used to confirm sleep state when determining whether the user is sleeping by comparing, the stored, sensor data representing the user's sleep state to current sensor data representing the user's current unknown state.

In some implementations, sleep logic 120 can predict future sleep periods. For example, sleep logic 120 can analyze the sleep history data in sleep history database. 134 to determine when the user usually sleeps. For example, if the user typically (e.g., historically has a pattern) sleeps between 11 pm and 7 am, then sleep logic 120 can predict that the user will go to sleep at 11 pm on the current day and/or future days.

Determining the Sleep Ritual

In some implementations, sleep logic 120 can determine the user's sleep ritual. For example, humans are creatures of habit. Most people have a specific set of activities that they perform before going to bed every night. For example, a user of computing device 102 may take the dog out, lock the front door, shut the window blinds, exercise, take a shower, and/or brush her teeth. These activities may not be done in the exact same order every night. The user may not perform every one of these activities every night. However, each night the user will perform at least some a subset) of these activities as part of the user's sleep ritual before she goes to bed. For example, if a user performs a particular activity at least a number of nights (e.g., 5, 6, at least 50%, etc.) per week, then sleep logic 120 can determine that the particular activity is a sleep ritual activity. These sleep ritual activities can be used to infer the user's intent to go to sleep.

In some implementations, sleep logic 120 can monitor sensor data before the user goes to sleep to determine the user's sleep ritual. For example, after sleep logic 120 determines the user's sleep patterns, as described above, sleep logic 120 can monitor the environment of computing device 102 to determine the user's activities right before the user is predicted to go to sleep. If sleep logic 120, for example, predicts that the user will go to sleep at 10 pm, for example, sleep logic 120 can turn on the sensors of computing device 102 before the user is predicted to go to sleep (e.g., 5 hour before, 1 hour before, 9:30 pm, etc.) to monitor or detect the user's bedtime activities (e.g., sleep ritual).

In some implementations, sleep logic 120 can monitor the environment of computing device 102 to determine the user's activities all the time or on regular intervals (e.g., every 2 minutes, every 5 minutes, etc.) throughout the day to detect and identify the user's activities. When sleep logic 120 determines that the user has gone to sleep, sleep logic 120 can analyze the user's activities to determine which activities were performed in a time period before the user went to sleep.

In some implementations, sleep logic 120 can identify sleep ritual activities using sound data generated by sound sensor 104. For example, various activities performed by the user as the user is preparing to go to sleep may generate noise or sounds that are detectable by sound sensor 104 and/or identifiable by sleep logic 120. Sleep logic 120, for example, can obtain sound samples (e.g., sound fingerprints) from a network resource (not shown) that have been mapped to corresponding activities that are known to have generated the sampled sounds. The sound samples can include the sound of someone brushing their teeth, adjusting window blinds, opening and closing doors, taking a shower, or any other activity that generates an identifiable or unique sound. The mapping of sounds to activities can be stored in sound database 132, for example. Thus, when the user brushes her teeth, the sound of the brushing can be detected by sound sensor 104 (e.g., microphone), and can be compared to the sounds in sound database 132 by sleep logic 120 to determine that the detected sound corresponds to the user brushing her teeth. After sleep logic 120 identifies the sound of the user brushing her teeth, the users tooth brushing activity can be added to the user's sleep ritual activities stored in sleep ritual database 130. Similarly, sound sensor 104 can detect and sleep logic 120 can identify sounds related to exercising, showering, closing window blinds, opening and closing doors, taking a dog outside, filling a glass with water, using the toilet, and/or any other sleep ritual activity. After a sleep ritual activity has been identified, sleep logic 120 can add the sleep ritual activity to sleep ritual database 130.

In some implementations, sleep logic 120 can identify sleep ritual activities using movement data generated by movement sensor 106. For example, various activities performed by the user as the user is preparing to go to sleep may generate motion or vibrations that are detectable by movement sensor 106 and/or identifiable by sleep logic 120. Sleep logic 120, for example, can obtain motion samples (e.g., motion fingerprints, patterns of motion) from a network resource (not shown) that have been mapped to corresponding activities that are known to have generated the sampled motion. The motion samples can include the motion of someone brushing their teeth (e.g., when wearing a smart watch), walking or exercising, or any other activity that generates motion or movement. The mapping of motion to activities can be stored in motion database 136, for example. Thus, when the user exercises before bed, the motion of the exercise can be detected by movement sensor 106 (e.g., accelerometer), and can be compared to the motion samples in motion database 136 by sleep logic 120 to determine that the detected motion corresponds to the user exercising. After sleep logic 120 identifies the motion of the user exercising, the user's exercise activity can be added to the user's sleep ritual activities stored in sleep ritual database 130. Similarly, movement sensor 106 can detect and sleep logic 120 can identify motion related to tooth brushing, and/or any other sleep ritual activity. After a sleep ritual activity has been identified, sleep logic 120 can add the sleep ritual activity to sleep ritual database 130.

In some implementations, sleep logic 120 can identify sleep ritual activities using light intensity data generated by light sensor 112. For example, humans normally like to sleep in a dark room. Thus, darkening the user's environment by drawing window shades or turning off a light can be part of the user's sleep ritual. When the user darkens the room before the predicted bedtime, light sensor 112 can detect the change in ambient light intensity and generate ambient light intensity data reflecting the change. Sleep logic 120 can analyze the light intensity data, determine that the ambient light intensity has been lowered, and determine that the user has darkened the room. Sleep logic 120 can store the darken room activity is sleep ritual database 130 as an activity that is part of the user's sleep ritual.

In some implementations, sleep logic 120 can identify sleep ritual activities based on application usage. For example, the user may have a habit of using specific software applications installed on computing device 102 immediately before going to bed. The user can check calendar application 140. The user can set a wake up alarm using alarm clock application 142. The user can use social media applications, news applications, a game application, an e-book reader application, and/or other applications before going to sleep. Sleep logic 120 can monitor application usage before the predicted sleep time (e.g., 1 hour before, 0.5 hour before, etc.) and determine, which applications the user uses before the user's predicted sleep time. Sleep logic 120 can store the detected application use activities as sleep ritual activities in sleep ritual database 130.

In some implementations, sleep logic 120 can identify sleep ritual activities based on state information received from secondary device 150. While FIG. 1 shows a single secondary device 150, system 100 can include multiple secondary devices 150. Secondary device 150 can be another computing device similar to computing device 102. Secondary device 150 can be a wearable device (e.g., smart watch, smart eye glasses, smart contacts, etc.). For example, secondary device 150 can detect and determine sleep ritual activities as described above and report the activities to in the state information sent to sleep logic 120 on computing device 102. Secondary device 150 can be a smart appliance or other networked device, such as a smart television, set top box, smart door lock, smart blinds, smart lamp, smart power grid, smart refrigerator, and/or some other home appliance.

In some implementations, secondary device 150 can report device state information to computing device 102. For example, secondary device 150 can connect to computing device 102 through network 160. For example, network 160 can be a local area network, wide area network, home Wi-Fi network, and/or the Internet. For example, sleep logic 120 determine which doors in the user's house are opened or closed, whether the blinds are opened or closed, whether a lamp is on or off, whether the refrigerator door is open or closed, what media the user is consuming, and/or other information based on state information received from secondary device 150.

Secondary device 150 can report device state information to computing device 120 periodically (e.g., every 5 minutes, every hour, etc.). Secondary device 150 can report device state information to computing device 120 in response to detecting a change in state of secondary device 150. For example, a change of state can be powering on or off the device, a user interacting with or manipulating the device, and/or any other user initiated device state change.

In some implementations, sleep logic 120 can store received device state information in sleep ritual database 130. For example, activities performed with respect to secondary device 150 can be part of the user's sleep ritual. Thus, when sleep logic 120 receives device state information from secondary device 150 that indicates a user interaction with secondary device 150 before the user goes to sleep, sleep logic 120 can store the interaction as a sleep ritual activity is sleep ritual database 130.

In some implementations, secondary device 150 can report device state information to sleep logic 120 in response to a request for state information received from computing device 120. For example, sleep logic 120 can determine that the user is about to go to sleep (e.g., the current time is near the user's predicted sleep time, the sleep logic 120 has determined that the user intends to sleep, etc.) and can request device state information from secondary device 150. Sleep logic 120 can store the received device state information in sleep history database 134 in the sleep record for the current sleep instance, as described above. Sleep logic 120 can analyze the device state information and compare the device state information with historical device state data to determine the typical (e.g., most frequently occurring over time) device state for each secondary device 150. The typical device state for each secondary device 150 can be stored as a sleep mode setting for the corresponding secondary device 150 in sleep mode settings database 138. For example, sleep logic 120 can use the device state information stored in sleep mode settings database 138 to automatically adjust the state or settings of secondary device 150 when the user goes to sleep, as described further below.

Determining Intent to Sleep

In some implementations, sleep logic 120 can determine that the user intends to sleep. For example, sleep logic 120 can present reminders about forgotten sleep ritual activities when sleep logic 120 determines that the user intends or is about to go to sleep. Sleep logic 120 can present reminders about secondary device settings or state (e.g., the oven is on, the light is on, etc.) when sleep logic 120 determines that the user intends to go to sleep.

In some implementations, the user's intent to sleep can be determined, based on detecting the user has performed the user's sleep ritual. For example, sleep logic 120 can monitor the activities of the user before the user's predicted sleep period using the sensors of computing device 102, as described above. Sleep logic 120 can identify the user's activities based on the sensor data, as described above, and compare the activities to the activities stored in sleep ritual database 130 to determine if the detected activity is part of the user's sleep ritual. Similarly, the user's sleep ritual can include adjustments to secondary device 150. If the user typically turns off a smart lamp, locks a smart lock, exercises while wearing a smart watch, opens a smart freezer, etc., before going to bed, these activities can be part of the user's sleep ritual. Sleep logic 120 can receive secondary device state information, identify the user's interactions or activities with respect to secondary device 150, and compare the activities to the activities stored in sleep ritual database 130 to determine if the detected activity is part of the user's sleep ritual.

Sleep logic 120 can determine that the user's sleep ritual was performed by the user when sleep logic 120 determines that a threshold number of the sleep ritual activities identified in sleep database 130 were performed. For example, sleep logic 120 can determine that the user is performing the user's sleep ritual when a minimum number (e.g., three or more) of the sleep ritual activities were performed in a short period of time (e.g., within 15 minutes, within 30 minutes, etc.). Sleep logic can determine that the user is performing the user's sleep ritual when a portion (e.g., greater than 30%, greater than 50%, etc.) of the sleep ritual activities were performed by the user in a short period of time.

In some implementations, sleep logic 120 can determine the user intends to go to sleep based on the time when the last of the user's sleep ritual activities is performed. If the user's sleep ritual (as indicated by the activities in sleep ritual database 130) includes the activities shower, brush teeth, darken the room, and set the wake up alarm for the next day, then, when the last of these activities is detected by computing device 102, sleep logic 120 can determine that the user intends to sleep. For example, if darkening the room is the last of the sleep ritual activities performed by the user and detected by light sensor 112 of computing device 102, then sleep logic 120 can determine that the user intends to go to sleep at the time at which darkening the room was detected.

In some implementations, sleep logic 120 can determine that the user intends to sleep based on heart rate data generated by heart rate sensor 108. For example, the user's heart rate may decrease in steps: first as a user prepares to sleep and again when the user is actually asleep. Thus, sleep logic 120 can include two heart rate thresholds: a first heart rate threshold for determining intent to sleep, and a second heart rate threshold for determining, when the user is sleeping. Heart rate sensor 108 can detect the user's heart rate, as described above, and send the heart rate data to sleep logic 120. Sleep logic 120 can compare the user's heart rate to the first and second heart rate thresholds. For example, if the user's heart rate is below the first heart rate threshold and above the second heart rate threshold, the user is preparing to sleep. If the user's heart rate is below the second heart rate threshold, the user is sleeping. Thus, sleep logic 120 can determine that the user intends to sleep when the user's heartrate drops below the first heart rate threshold. Sleep logic 120 can determine that the user is sleeping when the user's heartrate drops below the second heart rate threshold.

Similarly, the user's heart rate variability may decrease in steps: first when the user is awake and resting, second when the user intends to sleep, and third when the user is asleep. Thus, sleep logic 120 can include two heart rate variability thresholds for determining sleep onset latency: a first variability threshold for determining intent to sleep or the start of sleep onset latency, and a second variability threshold lower than the first variability threshold for determining when the user is sleeping. Heart rate sensor 108 can detect the user's heart rate, as described above, and send the heart rate data to sleep logic 102. Sleep logic 120 can compare the user's heart rate variability to the first and second variability thresholds. For example, if the user's heart rate variability is below the first variability threshold and above the second variability threshold, the user is preparing to sleep and has begun the sleep onset latency period. If the user's heart rate variability is below the second variability threshold, the user is sleeping. Thus, sleep logic 120 can determine the start of sleep onset latency when the user's heart rate variability drops below the first heart rate threshold. Sleep logic 120 can determine the end of sleep onset latency and the beginning of sleep when the user's heart rate variability drops below the second variability threshold.

In some implementations, sleep logic 120 can determine the user intends to sleep based on breathing rate data generated by breathing rate sensor 110. For example, the user's breathing rate may decrease in steps: first as a user prepares to sleep and again when the user is actually asleep. Thus, sleep logic 120 can include two breathing rate thresholds: a first breathing rate threshold for determining intent to sleep, and a second breathing rate threshold for determining when the user is sleeping. Breathing rate sensor 108 can detect the user's breathing rate, as described above, and send the breathing rate data to sleep logic 120. Sleep logic 120 can compare the user's breathing rate to the first and second breathing rate thresholds. For example, if the user's heart rate is below the first breathing rate threshold and above the second breathing rate threshold, the user is preparing to sleep. If the user's breathing rate is below the second breathing rate threshold, the user is sleeping. Thus, sleep logic 120 can determine that the user intends to sleep when the user's breathing drops below the first breathing rate threshold. Sleep logic 120 can determine that the user is sleeping when the user's breathing drops below the second breathing rate threshold.

Similarly, the user's breathing rate variability may decrease in steps: first as a user prepares to sleep and again when the user is actually asleep. Thus, sleep logic 102 can include two breathing variability thresholds: a first variability threshold for determining intent to sleep or the start of sleep onset latency, and a second variability threshold lower than the first variability threshold for determining when the user is sleeping. Breathing rate sensor 108 can detect the user's breathing rate, as described above, and send the breathing rate data to sleep logic 102. Sleep logic 102 can compare the user's breathing rate variability to the first and second variability thresholds. For example, if the user's breathing rate variability is below the first variability threshold and above the second variability threshold, the user is preparing to sleep and has begun the sleep onset latency period. If the user's breathing rate variability is below the second variability threshold, the user is sleeping. Thus, sleep logic 102 can determine the start of sleep onset latency when the user's breathing rate variability drops below the first variability threshold. Sleep logic 102 can determine the end of sleep onset latency and the beginning of sleep when the user's breathing rate variability drops below the second variability threshold. Similar thresholding logic can be used to determine sleep onset latency based on breathing amplitude, as described above.

In some implementations, sleep logic 120 can determine the user's intent to sleep based on user input detected by pressure sensor 114. For example, sleep logic 120 can use pressure sensor 114 to determine when the user intends to sleep and the start of sleep. Sleep logic 120 (or sleep application 146) can present a graphical user interface on a touch sensitive display of computing device 102. The graphical user interface can ask the user to apply and hold pressure on the display when the user intends to sleep. The pressure applied by the user can be detected by pressure sensor 114. Pressure sensor 110 can detect a high level of pressure initially. The amount of pressure detected by pressure sensor 110 will be reduced as the user falls asleep until little or no pressure is detected when the user is asleep. The pressure data generated by pressure sensor 114 can be analyzed by sleep logic 120 to determine when the user initially applied pressure (e.g., corresponding to the users intent to sleep) and when the user applied the least amount of pressure after the initial pressure was applied (e.g., corresponding to when the user fell asleep).

In some implementations, sleep logic 120 can determine the user's intent to sleep based on user input detected by touch sensor 116. For example, sleep logic 120 and/or sleep application 146 can provide a graphical user interface that allows the user to indicate that the user intends to go to sleep. The user can, for example, touch a button or graphical user interface element on a touch sensitive display to indicate the user's intent to go to sleep. Touch sensor 116 can detect the touch input and sleep logic 120 can determine that the user intends to sleep based on when the touch input was received.

Presenting Reminders

In some implementations, sleep logic 120 can present reminders to perform sleep ritual activities in response to determining that the user intends to sleep. For example, after sleep logic 120 determines the activities that are part of the user's sleep ritual, sleep logic 120 can remind the user to perform sleep ritual activities that the user may have forgotten to perform before going to bed. For example, sleep logic 120 can send a reminder message to notification process 144 and notification process 144 can present the reminder to the user on a graphical user interface of computing device 102. Notification process 144 can be an operating system process (e.g., utility or function) or a standalone application, for example. Sleep logic 120 can help the user sleep better by reminding the user to perform the activities before the user sleeps so that the user does not wake later with worry about missing one of the sleep ritual activities.

In some implementations, sleep logic 120 can determine when a user forgets to perform a sleep ritual activity. For example, sleep logic 120 can analyze sensor data, secondary devices data, network traffic, and/or other data to detect and identify activities that the user performs before going to bed, as described above. Sleep logic 120 can compare the detected activities (e.g., at the current time) to known sleep ritual activities stored in sleep ritual database 130 to determine whether the user has performed each of the sleep ritual, activities identified in sleep ritual database 130. When sleep logic 120 determines that the user intends to sleep (e.g., the user is done with pre-sleep activities), sleep logic 120 can determine which sleep ritual activities in sleep ritual database 130 the user has failed (e.g., forgotten) to perform before going to sleep (e.g., before going to bed) by determining which sleep ritual activities in sleep ritual database 130 were not detected. Sleep logic 120 can then present a reminder to the user to perform the forgotten sleep ritual activity. For example, the reminder can be presented in response to sleep logic 120 determining that the user intends to sleep (e.g., go to bed).

In some implementations, sleep logic 120 can remind the user to perform sleep ritual activities related to personal hygiene. For example, if sleep logic 120 has previously determined that the user brushes her teeth, uses the toilet, takes a shower, and/or performs some other personal hygiene activity as part of the user's sleep ritual, sleep logic 120 can remind the user to perform the personal hygiene activity so that the user's sleep is not later disturbed when the user wonders if she remembered to perform the activity or when nature calls.

In some implementations, sleep logic 120 can remind the user to perform sleep ritual activities related to personal security. For example, if sleep logic 120 has previously determined that the user typically locks a door, draws the window blinds, shuts or locks a window, or performs some other security related activity as part of the user's sleep ritual, sleep logic 120 can remind the user to perform the personal security activity so that the user's sleep is not later disturbed when the user wonders if she remembered to perform the security-related activity.

In some implementations, sleep logic 120 can remind the user to perform sleep ritual activities related to personal safety. For example, if sleep logic 120 has previously determined that the user typically turns off the oven or stove top, blows out candles, puts out the fire in the fireplace, unplugs a device, or performs some other safety related activity as part of the user's sleep ritual, sleep logic 120 can remind the user to perform the personal safety activity so that the user's sleep is not later disturbed when the user wonders if she remembered to perform the safety-related activity.

In some implementations, sleep logic 120 can remind the user to perform sleep ritual activities related to pets. For example, if sleep logic 120 has previously determined that the user typically takes the dog out, puts the dog in a kennel, fills the cat's water bowl, or performs some other pet-related activity as part of the user's sleep ritual, sleep logic 120 can remind the user to perform the pet activity so that the user's sleep is not later disturbed when the user wonders if she remembered to perform the pet-related activity.

In some implementations, sleep logic 120 can remind the user to perform sleep ritual activities related to energy conservation. For example, if sleep logic 120 has previously determined that the user typically turns off lights, lowers or raises the thermostat setting for the air conditioner, turns off the television, unplugs a personal computing device, and/or performs some other energy conservation related activity as part of the user's sleep ritual, sleep logic 120 can remind the user to perform the energy conserving, activity so that the user's sleep is not later disturbed when the user wonders if she remembered to perform the energy conservation related activity.

In some implementations, sleep logic 120 can remind the user to perform sleep ritual activities related to energy conservation. For example, if sleep logic 120 has previously determined that the user typically turns off lights, lowers or raises the thermostat setting for the air conditioner, turns off the television, unplugs a personal computing device, and/or performs some other energy conservation related activity as part of the user's sleep ritual, sleep logic 120 can remind the user to perform the energy conserving activity so that the user's sleep is not later disturbed when the user wonders if she remembered to perform the energy conservation related activity.

In some implementations, sleep logic 120 can remind, the user to perform sleep ritual activities related to the user's schedule. For example, if sleep logic 120 has previously determined that the user typically checks her calendar, sets an alarm, schedules a reminder, checks her email, program or turn on the coffee maker, and/or performs sonic other schedule related activity as part of the user's sleep ritual, sleep logic 120 can remind the user to perform the scheduling activity so that the user's sleep is not later disturbed when the user wonders what is on her schedule the next day, or wonders if she remembered to perform some schedule related activity. If sleep logic 120 has previously determined that the user typically plugs computing device 102 into a charging device to recharge the battery of computing device 102 before going to sleep, sleep logic 120 can present a reminder to remind the user to connect computing device 102 to the charger.

Figure 2:
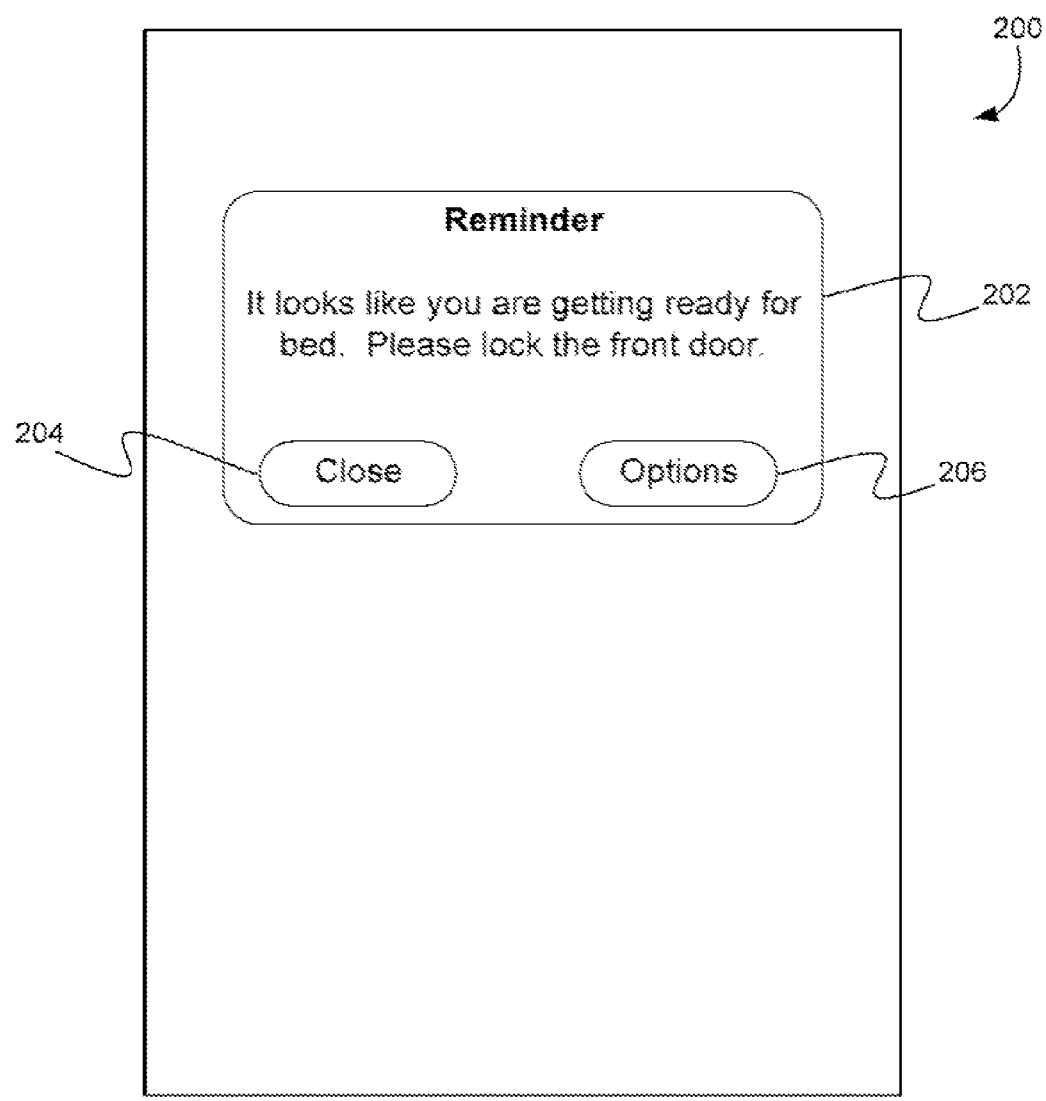
FIG. 2 illustrates an example graphical user interface 200 for reminding the user to perform a sleep ritual activity.

FIG. 2 illustrates an example graphical user interface 200 for reminding the user to perform a sleep ritual activity. For example, graphical user interface (GUI) 200 can include notification 202. Notification 202 can be a graphical element presented on GUI 200 that includes a message, such as a reminder. Notification 202 can be a graphical element generated by notification process 144, for example. Notification 202 can be presented when sleep logic 120 determines that the user intends to go to sleep and/or that the user failed to perform one or more of the user's sleep ritual activities. For example, in response to determining that the user intends to go to sleep and that the user failed to perform a sleep ritual activity, sleep logic 120 can cause notification 202 to be presented on GUI 200 to remind the user to perform the sleep ritual activity before going to sleep.

In some implementations, notification 202 can include a description of the sleep ritual activity that the user failed to perform. For example, if the sleep logic 120 determined that the user failed to lock the front door, or turn off a light, or brush her teeth, notification 202 can include a description of the sleep activity and a reminder to perform the missed sleep ritual activity. In some implementations, notification 202 can include graphical element 204. For example, graphical element 204 can be a virtual button or other selectable element. When the user selects graphical element 204, notification 202 can be dismissed (e.g., removed from view on GUI 200).

In some implementations, notification 202 can include graphical element 206. For example, graphical element 206 can be a virtual button or other selectable element. When the user selects graphical element 206, options associated with the reminder can be presented to the user. In some implementations, the options can include performing an action with respect to the reminder. For example, if the reminder reminds the user to turn of a smart lamp, the user can select an option to remotely turn off the smart lamp using computing device 102. For example, computing device 102 can send a message to the smart lamp through a network connection to the smart lamp to cause the smart lamp to turn off. In some implementations, the options can include an option to prevent future reminders for the sleep ritual activity. For example, if the reminder reminds the user to take a shower, the user may not wish to be reminded to shower before bed and can select an option to prevent future reminders to shower before bed. If the user selects this option to prevent future reminders about showering, sleep logic 120 will not remind the user to shower in the future.

Figure 3:
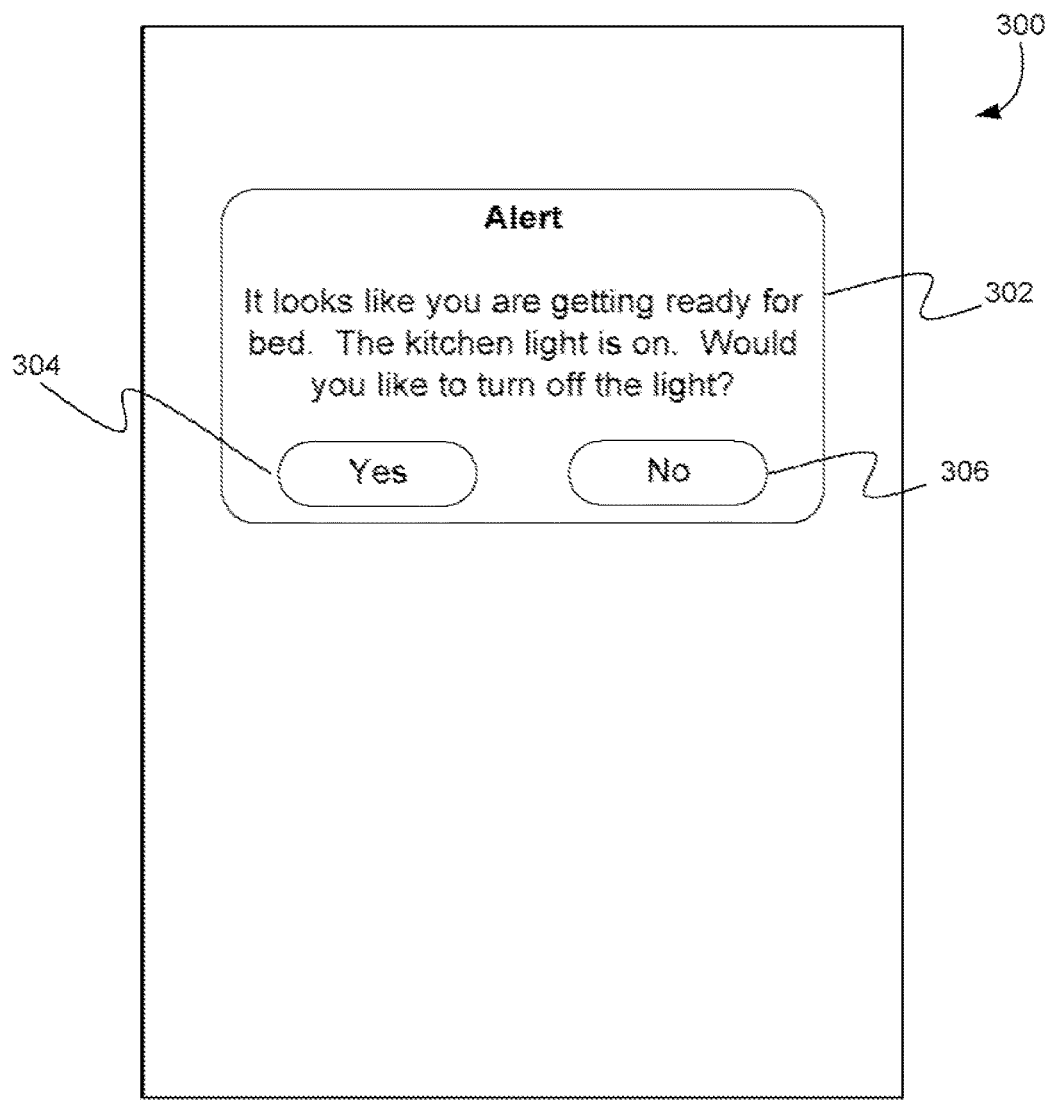
FIG. 3 illustrates an example graphical user interface 300 for alerting a user to the state of a secondary device.

FIG. 3 illustrates an example graphical user interface 300 for alerting a user to the state of a secondary device. For example, GUI 300 can include notification 302. Notification 302 can be a graphical element presented on GUI 300 that includes a message, such as an alert or reminder. Notification 302 can be a graphical element generated by notification process 144, for example. Notification 302 can be presented when sleep logic 120 determines that the user intends to go to sleep and/or that the user failed to perform one or more of the user's sleep ritual activities. For example, in response to determining that the user intends to go to sleep and that the user failed to perform a sleep ritual activity, sleep logic 120 can cause notification 302 to be presented on GUI 300 to remind the user to perform the sleep ritual activity before going to sleep.

In some implementations, notification 302 can present an alert notifying the user of the state of a secondary device. As described above, sleep logic 120 can determine sleep settings for secondary devices, such as smart appliances or other computing devices and store the sleep settings in sleep mode settings database 138. When sleep logic 120 determines that the user intends to sleep, sleep logic 120 can request state information from the various secondary devices of the user. In response to the request, the secondary devices (e.g., smart lamps, smart door locks, smart televisions, etc.) can send information describing the current state of the secondary devices to sleep logic 120. Sleep logic 120 can compare the current state of the secondary devices to the secondary device settings (e.g., user's desired sleep settings) stored in sleep mode settings database 138 to determine if the current state of the devices matches the sleep mode settings. When the current state of a secondary device does not match or correspond to the sleep mode setting for the device is sleep mode database 138, sleep logic 120 can cause notification process 144 to present notification 302 to alert the user to the state of the secondary device. For example, if a smart oven sends state information to sleep logic 120 indicating that the oven is turned on and the sleep mode settings database 138 indicates that the oven should be turned off, sleep logic 120 can cause notification 302 to be presented on GUI 300 alerting the user to the fact that the oven is still on.

In some implementations, notification 302 can include graphical element 304. For example, graphical element 304 can be a selectable element (e.g., a button) that the user can select to cause a secondary device to change state to the desired state indicated for the secondary device in sleep mode settings database 138. For example, if notification 302 presents an alert to the user indicating that a smart light fixture is on and the sleep mode settings database 138 indicates that the smart light fixture should be turned off when the user goes to sleep, the user can select graphical element 304 to cause computing device 102 to send a message to the smart light fixture to cause the smart light fixture to turn off. In some implementations, notification 302 can include graphical element 306. For example, a user can select graphical element 306 to dismiss notification 302 without causing computing device 102 to take any additional action related to the secondary device identified by notification 302.

Figure 4:
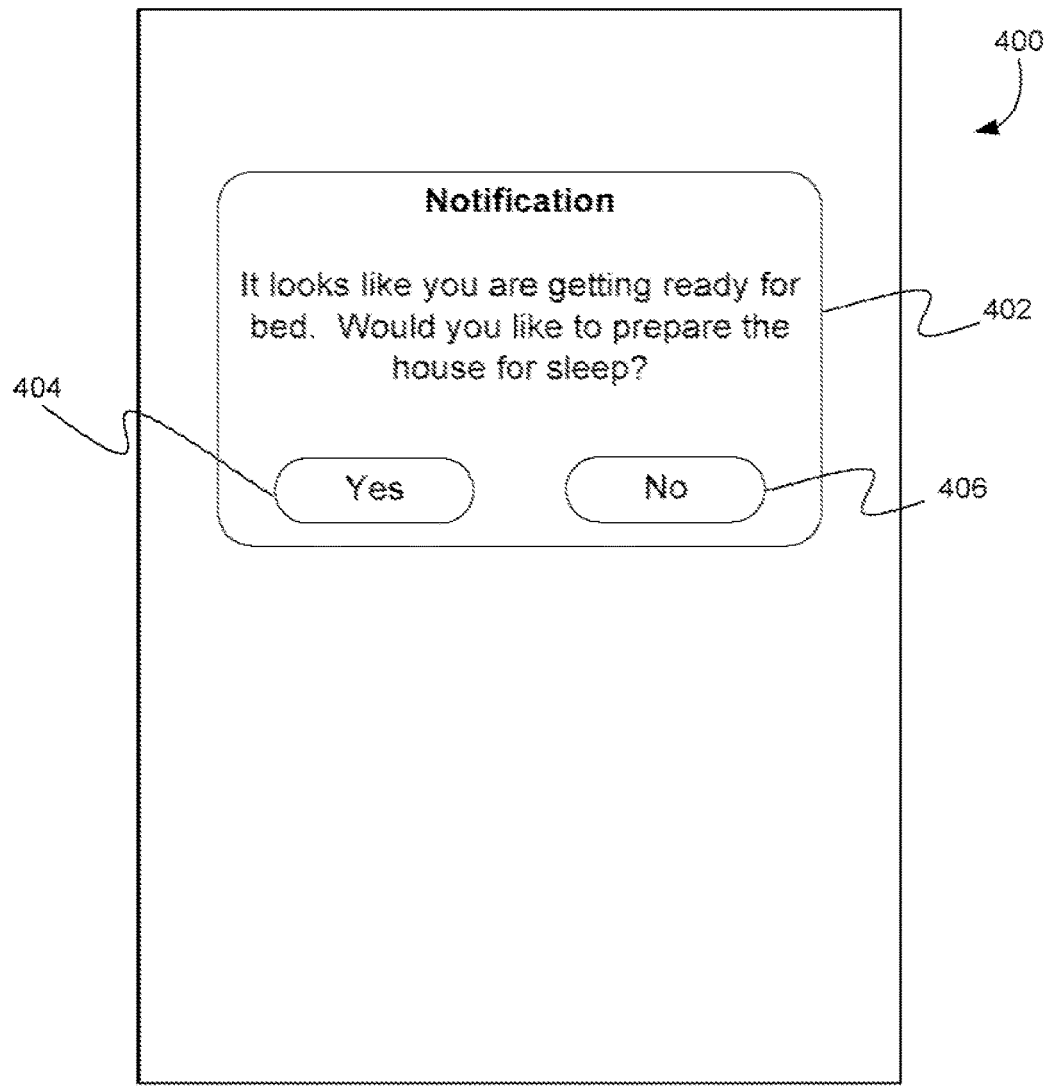
FIG. 4 illustrates an example graphical user interface 400 for automatically adjusting secondary devices for sleep.

FIG. 4 illustrates an example graphical user interface 400 for automatically adjusting secondary devices for sleep. For example, GUI 400 can include notification 402. Notification 402 can be a graphical element presented on GUI 400 that includes a message, such as a prompt. Notification 402 can be a graphical element generated by notification process 144, for example. Notification 402 can be presented when sleep logic 120 determines that the user intends to go to sleep. For example, in response to determining that the user intends to go to sleep, sleep logic 120 can cause notification 402 to be presented on GUI 300 to prompt the user to provide input indicating that the user would like computing device 102 to change the state of secondary devices in preparation for the user to sleep.

In some implementations, notification 402 can include graphical element 404. For example, graphical element 404 can be a selectable graphical element (e.g., a button) that when selected by a user causes computing device 102 to change the state of secondary devices to the desired states specified (e.g., identified) in sleep mode database 138. For example, when sleep logic 120 determines that the user intends to sleep, sleep logic 120 can cause notification process 144 to present notification 402 asking (e.g., prompting) the user if the user would like computing device 102 to prepare the user's house (e.g., secondary devices in the house) for sleep. When the user responds affirmatively by selecting graphical element 404, sleep logic 120 can obtain the user's desired sleep settings for the secondary devices from sleep mode database 138. Sleep logic 120 can send a message to each secondary device indicating the desired sleep mode setting for the respective secondary device. In response to receiving the message, each secondary device can change its state to match the desired sleep mode setting. For example, if the desired sleep mode setting for the oven is "off", sleep logic can send a message to the oven indicating the "off" state. When the oven receives the message, the oven can turn itself off if it is in the "on" state or take no action if the oven is already off. A similar process can be used to adjust the state of smart televisions, smart door locks, smart window shades or blinds, smart light fixtures, or any other smart computerized, networked, etc.) home device or appliance.

In some implementations, sleep logic 120 can present a graphical user interface that presents the current state of the secondary devices. For example, when sleep logic 120 determines that the user intends to sleep, sleep logic 120 can present a graphical user interface that presents the current state of each of the user's secondary devices (e.g., smart devices, smart appliances, etc.). Thus, even if each secondary device is already in the appropriate sleep state, the user can be reassured that the state of each device is as the user desires before going to sleep.

Example Processes

Figure 5:
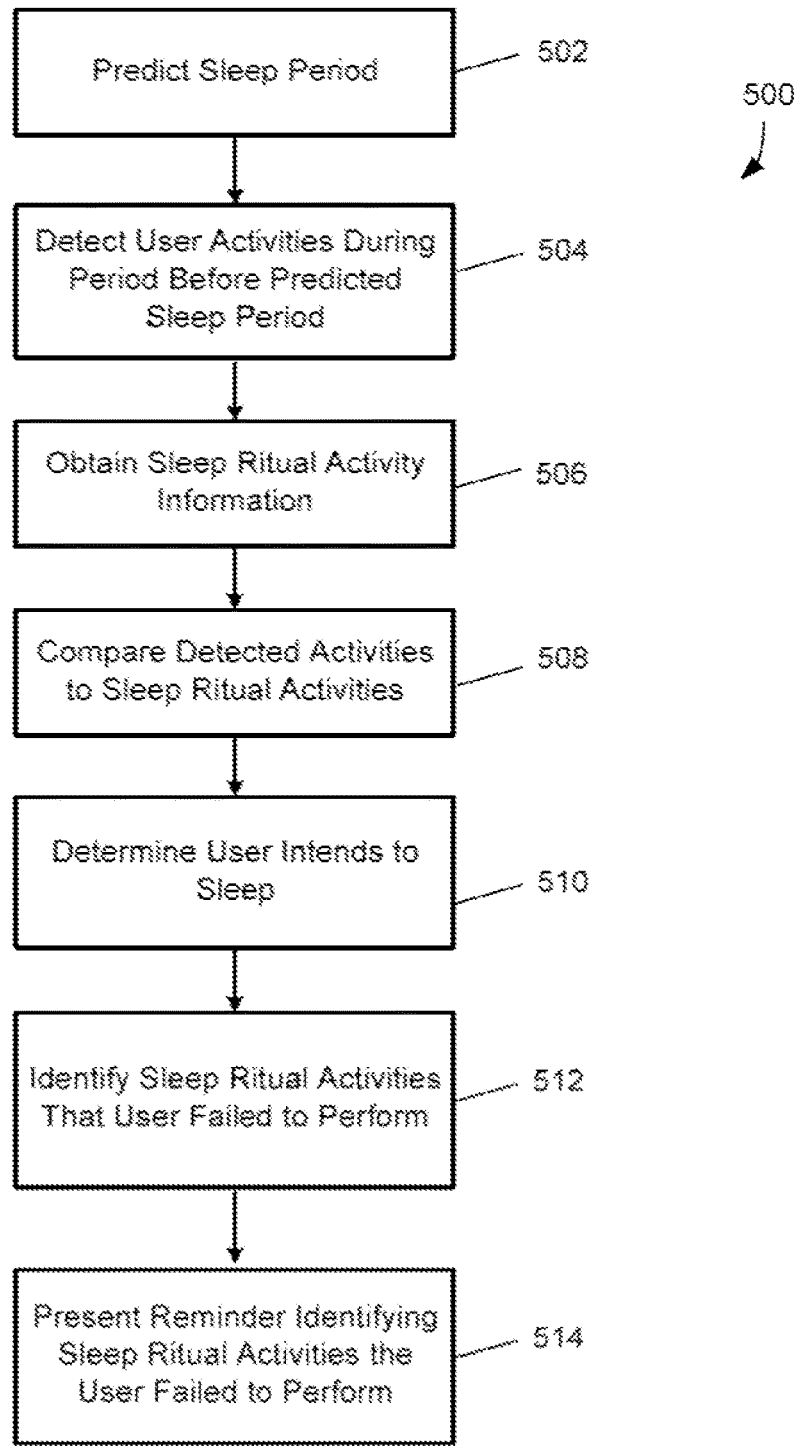
FIG. 5 is flow diagram of an example process 500 for facilitating restful sleep using reminders.

FIG. 5 is flow diagram of an example process 500 for facilitating restful sleep using reminders. For example, process 500 can help a user get a restful night's sleep by reminding the user to perform activities before going to sleep that the user might think about after later and that might cause the user to wake or get out of bed.

At step 502, computing device 102 can predict a user's sleep period. For example, computing device 102 can obtain historical sensor data that corresponds to the user sleeping. Computing device 102 can obtain historical use data that indicates time periods when the user is using and/or is not using computing device 102. Based on the historical data, computing device 102 can predict when the user will sleep in the future. For example, computing device 102 can predict when (e.g., what time) the user will go to sleep and/or when the user will wake up.

At step 504, computing device 102 can detect user activities during a period of time before the predicted sleep period. For example, computing device 102 can receive sensor data, secondary device state information, primary device use information describing the user's use of computing device 102, and/or other information describing the user's activities during a period of time (e.g., 30 minutes, 1 hour, etc.) immediately before a time when the user is predicted to go to sleep. Based on the information, computing device 102 can identify the activities performed by the user before the user goes to sleep.

At step 506, computing device 102 can obtain sleep ritual activity information. For example, a sleep ritual activity is an activity that is regularly performed by the user night after night. The user may not perform a sleep ritual activity every night but the user will perform a sleep ritual activity most nights. For example, if the user performs an activity before going to sleep at least 80% (e.g., some threshold percentage) of the time, computing device 102 can identify the activity as a sleep ritual activity. If the user performs an activity before going to sleep at least 6 nights (e.g., some threshold number) a week, computing device 102 can identify the activity as a sleep ritual activity. Computing device 102 can determine and store sleep ritual activities and associated data (e.g., sound samples, sensor data, device state information, etc.) in sleep ritual database 130, for example. Computing device 102 can obtain the sleep ritual activity information from sleep ritual database 130 when determining whether to present reminders to the user.

In some implementations, computing device 102 can associate a sleep ritual with a particular location. For example, a user may perform a particular sleep ritual when at home and a different sleep ritual when traveling (e.g., away from home, at a hotel, visiting friends, etc.). Computing device 102 can determine the current location of the user and obtain sleep ritual information corresponding to the "home" location and a sleep ritual corresponding the "away from home" location.

At step 508, computing device 102 can compare the detected activities to the sleep ritual activities. For example, computing device 102 can compare the activities detected at step 504 to the sleep ritual activity information obtained at step 506 to determine which sleep ritual activities have been performed and which sleep ritual activities have not been performed. For example, computing device 102 can continue performing steps 504, 506, and 508 until computing device 102 determines that the user intends to go to sleep at step 510.

At step 510, computing device 102 can determine that the user intends to sleep. In some implementations, computing device 102 can determine that the user intends to sleep when the user has performed at least a threshold number (e.g., 60%, 7 out of 10, etc.) of sleep ritual activities. In some implementations, the threshold number can be adjusted based on the user's sleep location. For example, most people adjust their sleep ritual based on location. A user at home will typically perform more sleep ritual activities than a user who is away from home. Thus, if the user is at home, the threshold number of sleep ritual activities can be higher (e.g., 80%). If the user is away from home, the threshold number of sleep ritual activities can be lower (e.g., 60%). In some implementations, computing device 102 can determine that the user intends to sleep when a period of time has passed (e.g., 10 minutes) after the user has performed the last of the detected sleep ritual activities. In some implementations, computing device 102 can determine that the user intends to sleep based on sensor data. For example, computing device 102 can use motion data, heart rate data, breathing rate data, sound data, and/or any other data to determine that the user intends to sleep, as described above.

At step 512, computing device 102 can identify sleep ritual activities that the user failed to perform. For example, based on the comparison of the detected activities to the sleep ritual activities at step 508, computing device 102 can determine which sleep ritual activities were performed by the user and which sleep ritual activities were not performed by the user.

At step 514, computing device 102 can present a reminder identifying the sleep ritual activities that the user failed to perform. For example, computing device 102 can present a single reminder that identifies all sleep ritual activities the user failed to perform. Computing device 102 can present a distinct (e.g., multiple, individual) reminder for each sleep ritual activity the user failed to perform. For example, computing device 102 can present reminders similar to the reminders illustrated by FIG. 2, FIG. 3 and/or FIG. 4.

Figure 6:
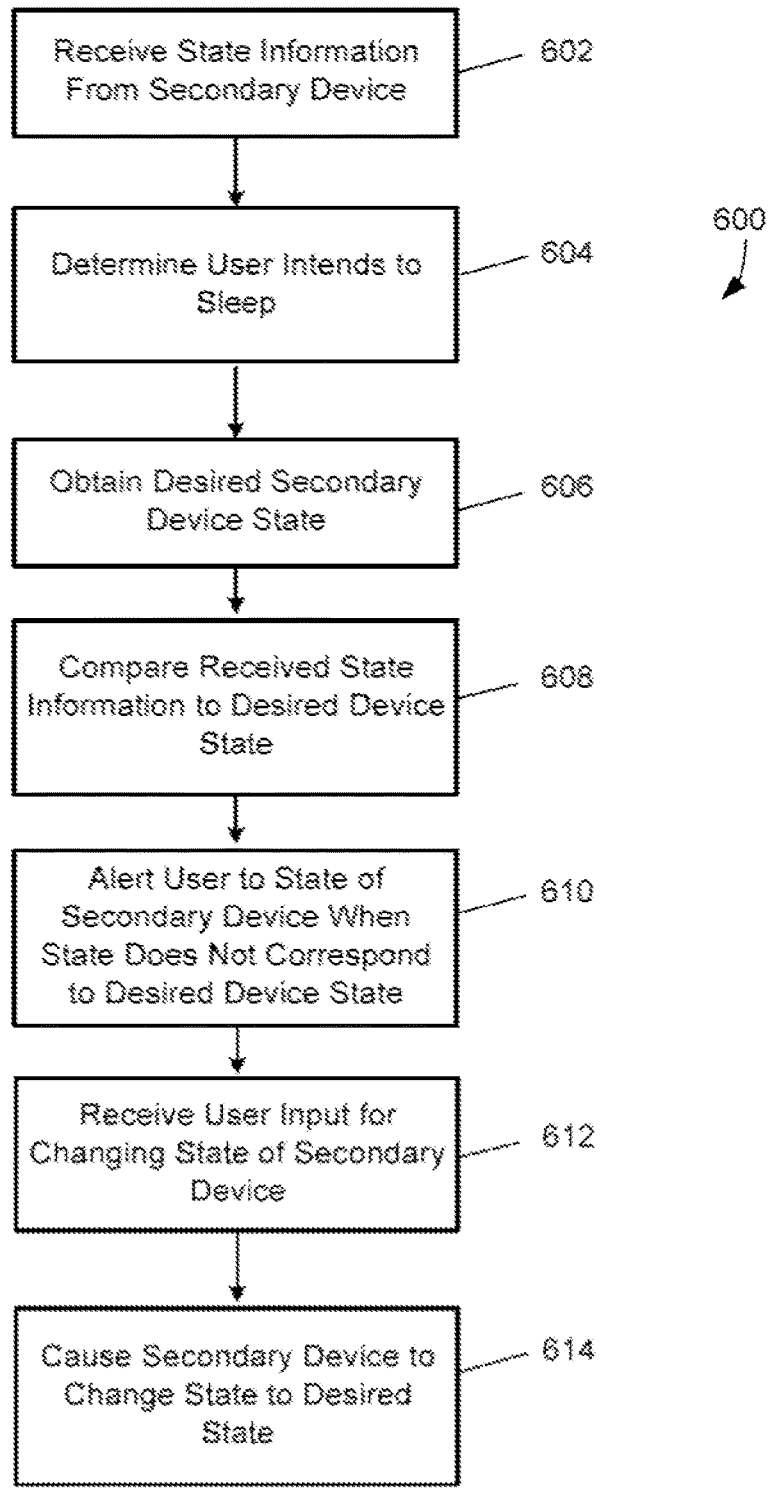
FIG. 6 is a flow diagram of an example process 600 for changing the state of a secondary device based on a user's desired device sleep state.

FIG. 6 is a flow diagram of an example process 600 for changing the state of a secondary device based on a user's desired device sleep state. For example, a user may desire that secondary devices (e.g., appliances, computers, fixtures, televisions, etc.) be in a particular operational state while the user sleeps. The user may want the oven turned off, the blinds closed, the front door locked, the television off, the thermostat set to a particular temperature, etc., while the user sleeps to ensure that the user is secure from intruders, safe from fire hazards, and/or conserving energy, among other reasons. Process 600 can help the user get a restful night sleep by checking the state of these secondary devices and providing a quick way for the user to change the state of a device to the user's desired state of the device while the user is sleeping.

At step 602, computing device 102 can receive device state information from a secondary device. For example, the device state information can describe (e.g., indicate) the current state of the secondary device. The device state information can indicate that the device is powered on, powered off and/or in a low power state. The device state information can indicate functions or operations being performed by the secondary device (e.g., playing media) and/or describe metadata associated with the function (e.g., identification of media played, type of media, channel or source for media, etc.). The device state information can indicate whether the secondary device is currently being used by the user. If the secondary device is a door lock, blinds, refrigerator, etc., the device state information can indicate whether the door is locked/unlocked, the blinds are open/closed, the refrigerator door is open/closed, and/or any other information describing the state of the secondary device.

At step 604, computing device 102 can determine that the user intends to sleep. For example, computing device 102 can determine that the user intends to sleep using the mechanisms, functions, features and/or data described above.

At step 606, computing device 102 can obtain the user's desired secondary device state. For example, the user's desired secondary device state can be determined based on historical device state information received from secondary devices. For example, computing device 102 can analyze the historical device state information and determine the most frequently occurring, device state for each secondary device at a time when the user is sleeping. Since the user will normally adjust the state of secondary devices before going to sleep (e.g., turn off lights, turn of oven, set thermostat, lock doors, etc.), the user's desired device state should be reflected in the historical device state data as the most frequently recorded device state for each secondary device. Computing device 102 can store the determined desired device state in sleep mode settings database 130 for later reference.

At step 608, computing device 102 can compare the received state information to the desired device state. For example, computing device can compare the secondary device state information received at step 602 to the desired secondary device state obtained at step 606 to determine if the current state of the secondary devices corresponds to the device state that the user desires the secondary devices to have while the user is sleeping.

At step 610, computing device 102 can alert the user to the state of a secondary device when the current state of the secondary device does not correspond to the desired device state. For example, when the current state of a secondary device does not corresponds to or match the device state that the user desires the secondary device to have while the user is sleeping, computing device 102 can present an alert to the user describing the current state of the secondary device. In some implementations, the alert can present an option the user can select to cause the secondary device to change to the desired device state.

At step 612, computing, device 102 can cause the secondary device to change state to the desired device state. For example, the user can provide input to the alert presented at step 610 to select the option to change the state of the secondary device to the user's desired device state. In response to receiving the user input, computing device 102 can send a message to the secondary device identifying the desired device state and requesting that the secondary device change state to the desired device state. In response to receiving the request, the secondary device can change the state of the secondary device to the desired device state. For example, when computing device 102 determines that the smart lock on the front door of the user's house is in the "unlocked" state and that the user's desired state for the smart lock is "locked," then when the user selects the option to change the state of the smart door lock to locked, computing device 102 can send a message to the smart lock to cause the smart lock to lock the front door. Thus, computing device 102 can help the user get a restful night sleep by alerting the user to secondary device states that do not match the user's desired states for the secondary devices.

Figure 7:
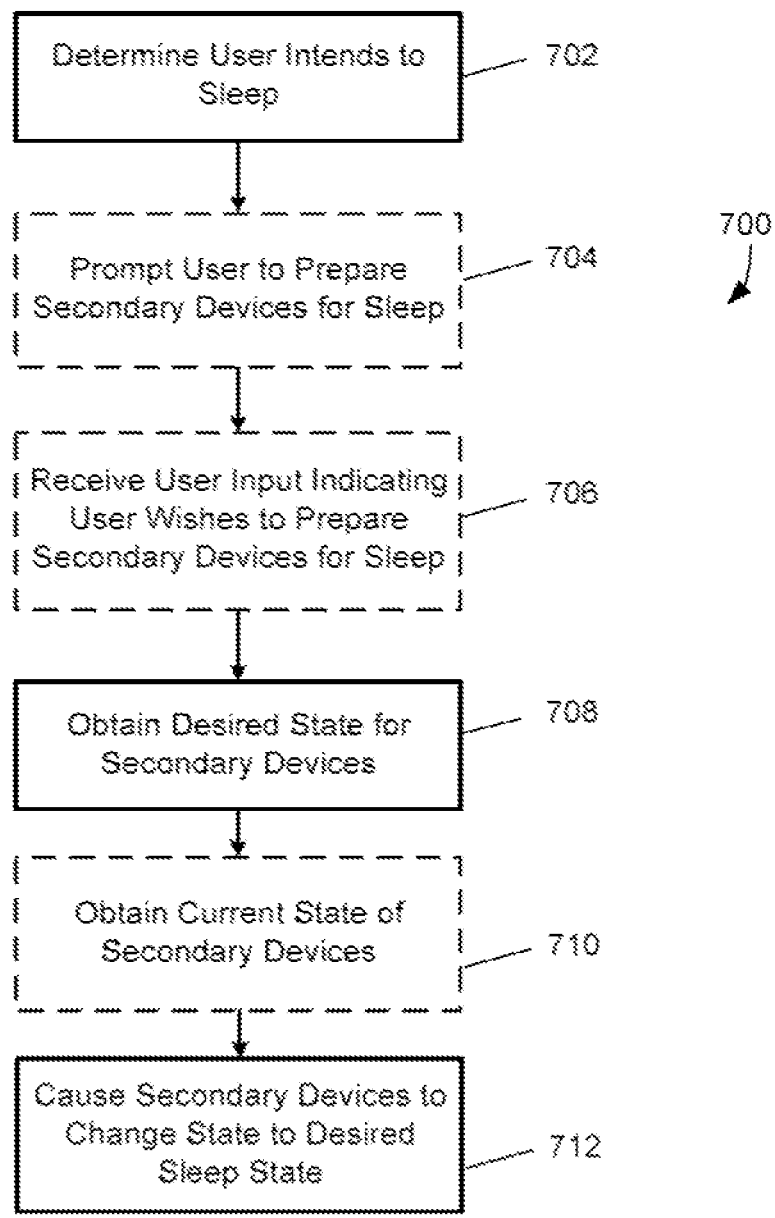
FIG. 7 is a flow diagram of an example process 700 for automatically preparing a plurality of secondary devices for sleep.

FIG. 7 is a flow diagram of an example process 700 for automatically preparing a plurality of secondary devices for sleep. For example, computing device 102 can be configured to automatically configure the state of the user's secondary devices based on the device state desired by the user for each secondary device while the user is sleeping.

At step 702, computing device 102 can determine that the user intends to sleep. For example, computing device 102 can determine that the user intends to sleep according to the mechanisms, processes, and/or data described above.

At step 704, computing device 102 can prompt the user to prepare the user's secondary devices for sleep. For example, computing device 102 can present a prompt that asks the user whether the user would like to set the user's secondary devices to the user's desired sleep state.

At step 706, computing device 102 can receive user input indicating that the user would like to prepare the user's secondary devices for sleep. For example, the user can select a graphical element (e.g., a button) to indicate to computing device 102 that the user would like computing device 102 to cause the secondary devices to assume the user's desired device state.

At step 708, computing device 102 can obtain the user's desired device state for the secondary devices. For example, computing device 102 can determine the user's desired device state based on historical device state information, as described above. Computing device 102 can obtain the user's desired device state from sleep mode settings database 138.

At step 710, computing device 102 can obtain the current state of the secondary devices. For example, in response to determining that the user intends to sleep, computing device 102 can send a request to each secondary device requesting the current state of each secondary device. In response to the request, each secondary device can send its current state information to computing device 102.

At step 712, computing device 102 can cause the secondary devices to change state to the desired sleep state. For example, after computing device 102 receives the current state of each secondary device, computing device 102 can identify which secondary devices have a current state that does not match the user's desired device state. Computing device can send a message to each identified secondary device requesting that the secondary device change its current state to the user's desired device state.

In some implementations, computing device 102 can perform process 700 without performing step 710. When computing device 102 performs process 700 without performing step 710, computing device 102 can send a message to each secondary device identifying the user's desired device state for the respective secondary device and requesting that the secondary devices adopt (e.g., change state to) the desired device state.

In some implementations, computing device 102 can perform process 700 without user input. For example, computing device 102 can perform process 700 without performing step 704 and step 706. In this case, computing device 102 will automatically (e.g., without user input) cause each secondary device to change its current state to the user's desired device state in response to determining that the user intends to go to sleep at step 702.

The steps of the processes described herein are described in a particular order for simplicity and to improve readability and understanding of the processes described. However, in some implementations, the steps of the processes can be performed in a different order and/or some of the steps of the processes can be omitted and/or new steps can be added while still producing similar results.

Example System Architecture

Figure 8:
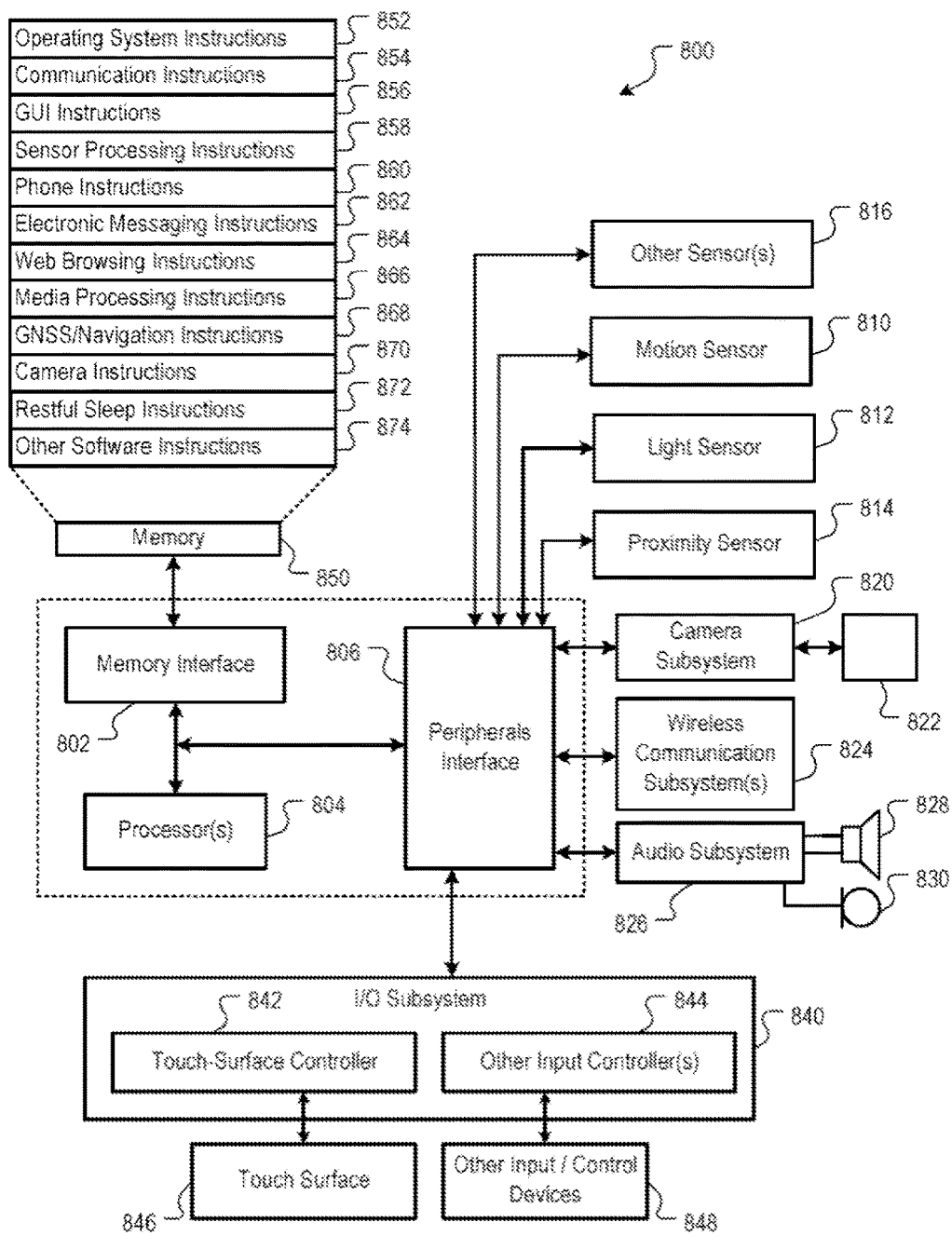
FIG. 8 is a block diagram of an example computing device 800 that can implement the features and processes of FIGS. 1-7.

FIG. 8 is a block diagram of an example computing device 800 that can implement the features and processes of FIGS. 1-7. The computing device 800 can include a memory interface 802, one or more data processors, image processors and/or central processing units 804, and a peripherals interface 806. The memory interface 802, the one or more processors 804 and/or the peripherals interface 806 can be separate components or can be integrated in one or more integrated circuits. The various components in the computing device 800 can be coupled by one or more communication buses or signal lines.

Sensors, devices, and subsystems can be coupled to the peripherals interface 806 to facilitate multiple functionalities. For example, a motion sensor 810, a light sensor 812, and a proximity sensor 814 can be coupled to the peripherals interface 806 to facilitate orientation, lighting, and proximity functions. Other sensors 816 can also be connected to the peripherals interface 806, such as a global navigation satellite system (GNSS) (e.g., GPS receiver), a temperature sensor, a biometric sensor, magnetometer or other sensing device, to facilitate related functionalities.

A camera subsystem 820 and an optical sensor 822, a charged coupled device (CCD) or a complementary metal-oxide semiconductor (CMOS) optical sensor, can be utilized to facilitate camera functions, such as recording photographs and video clips. The camera subsystem 820 and the optical sensor 822 can be used to collect images of a user to be used during authentication of a user, e.g., by performing facial recognition analysis.

Communication functions can be facilitated through one or more wireless communication subsystems 824, which can include radio frequency receivers and transmitters and/or optical (e.g., infrared) receivers and transmitters. The specific design and implementation of the communication subsystem 824 can depend on the communication network(s) over which the computing device 800 is intended to operate. For example, the computing device 800 can include communication subsystems 824 designed to operate over a GSM network, a GPRS network, an EDGE network, a Wi-Fi or WiMax network, and a Bluetooth™ network. In particular, the wireless communication subsystems 824 can include hosting protocols such that the device 100 can be configured as a base station for other wireless devices.

An audio subsystem 826 can be coupled to a speaker 828 and a microphone 830 to facilitate voice-enabled functions, such as speaker recognition, voice replication, digital recording, and telephony functions. The audio subsystem 826 can be configured to facilitate processing voice commands, voiceprinting and voice authentication, for example.

The I/O subsystem 840 can include a touch-surface controller 842 and/or other input controller(s) 844. The touch-surface controller 842 can be coupled to a touch surface 846. The touch surface 846 and touch-surface controller 842 can, for example, detect contact and movement or break thereof using any of a plurality of touch sensitivity technologies, including but not limited, to capacitive, resistive, infrared, and surface acoustic wave technologies, as well as other proximity sensor arrays or other elements for determining one or more points of contact with the touch surface 846.

The other input controller(s) 844 can be coupled to other input/control devices 848, such as one or more buttons, rocker switches, thumb-wheel, infrared port, USB port, and/or a pointer device such as a stylus. The one or more buttons (not shown) can include an up/down button for volume control of the speaker 828 and/or the microphone 830.

In one implementation, a pressing of the button for a first duration can disengage a lock of the touch surface 846; and a pressing of the button for a second duration that is longer than the first duration can turn power to the computing device 800 on or off. Pressing the button for a third duration can activate a voice control, or voice command, module that enables the user to speak commands into the microphone 830 to cause the device to execute the spoken command. The user can customize a functionality of one or more of the buttons. The touch surface 846 can, for example, also be used to implement virtual or soft buttons and/or a keyboard.

In some implementations, the computing device 800 can present recorded audio and/or video files, such as MP3, AAC, and MPEG files. In some implementations, the computing device 800 can include the functionality of an MP3 player, such as an iPod™. The computing device 800 can, therefore, include a 36-pin connector that is compatible with the iPod. Other input/output and control devices can also be used.

The memory interface 802 can be coupled to memory 850. The memory 850 can include high-speed random access memory and/or non-volatile memory, such as one or more magnetic disk storage devices, one or more optical storage devices, and/or flash memory (e.g., NAND, NOR). The memory 850 can store an operating system 852, such as Darwin, RTXC, LINUX, UNIX, OS X, WINDOWS, or an embedded operating system such as VxWorks.

The operating system 852 can include instructions for handling basic system services and for performing, hardware dependent tasks. In some implementations, the operating system 852 can be a kernel (e.g., UNIX kernel). For example, operating system 852 can implement the restful sleep features as described with reference to FIGS. 1-7.

The memory 850 can also store communication instructions 854 to facilitate communicating with one or more additional devices, one or more computers and/or one or more servers. The memory 850 can include graphical user interface instructions 856 to facilitate graphic user interface processing; sensor processing instructions 858 to facilitate sensor-related processing and functions; phone instructions 860 to facilitate phone-related processes and functions; electronic messaging instructions 862 to facilitate electronic-messaging related processes and functions; web browsing instructions 864 to facilitate web browsing-related processes and functions; media processing instructions 866 to facilitate media processing-related processes and functions; GNSS/Navigation instructions 868 to facilitate GNSS and navigation-related, processes and instructions; and/or camera instructions 870 to facilitate camera-related processes and functions.

The memory 850 can store other software instructions 872 to facilitate other processes and functions, such as the restful sleep processes and functions as described with reference to FIGS. 1-7.

The memory 850 can also store other software instructions 874, such as web video instructions to facilitate, web video-related processes and functions; and/or web shopping instructions to facilitate web shopping-related processes and functions. In some implementations, the media processing instructions 866 are divided into audio processing instructions and video processing instructions to facilitate audio processing-related processes and functions and video processing-related processes and functions, respectively.

Each of the above identified instructions and applications can correspond to a set of instructions for performing one or more functions described above. These instructions need not be implemented as separate software programs, procedures, or modules. The memory 850 can include additional instructions or fewer instructions. Furthermore, various functions of the computing device 800 can be implemented in hardware and/or in software, including in one or more signal processing and/or application specific integrated circuits.

What is claimed is:

1. A method comprising:
   detecting, by a computing device, user activities during a first period of time, the detecting comprising:
   receiving device state information from a secondary device through a network interface device of the computing device; and
   identifying the user activities based on the received device state information;
   obtaining, by the computing device, sleep ritual activity information corresponding to the user, the sleep ritual activity information identifying a plurality of historical sleep ritual activities that the user historically performs before sleeping;
   comparing, by the computing device, the detected user activities to the historical sleep ritual activities to produce a comparison;
   determining, by the computing device, that the user intends to sleep at a current time based on the comparison;
   in response to determining that the user intends to sleep at the current time, identifying, by the computing device, one or more particular sleep ritual activities of the historical sleep ritual activities that the user has failed to perform within the first period of time based on the comparison; and
   causing, by the computing device, a reminder notification to be presented on a display of the computing device that identifies the one or more particular sleep ritual activities the user failed to perform.

2. The method of claim 1, wherein the historical sleep ritual activities include use of the secondary device, and wherein the reminder notification reminds the user to use the secondary device to change a device state of the secondary device prior to sleeping.

3. The method of claim 1, wherein the historical sleep ritual activities include a personal hygiene activity, and wherein the reminder notification reminds the user to perform the personal hygiene activity prior to sleeping.

4. The method of claim 1, wherein the historical sleep ritual activities include a personal security activity, and wherein the reminder notification reminds the user to perform the personal security activity prior to sleeping.

5. The method of claim 1, wherein the historical sleep ritual activities include an energy conservation activity, and wherein the reminder notification reminds the user to perform the energy conservation activity prior to sleeping.

6. The method of claim 1, wherein detecting the user activities comprises:
   receiving sensor data from one or more sensor devices of the computing device; and
   identifying the user activities based on the received sensor data.

7. The method of claim 1, wherein detecting the user activities comprises:
   obtaining a plurality of motion samples and storing at least some of the plurality of motion samples to a motion database, each motion sample being mapped to a corresponding activity;
   detecting motion of the computing device using one or more motion sensors of the computing device; and
   identifying the user activities based on a comparison of the detected motion to motion samples stored to the motion database.

8. The method of claim 1, wherein the identified historical sleep ritual activities include the user setting a secondary device to a particular state, and wherein the reminder notification reminds the user to change a current state of the secondary device to the particular state prior to sleeping.

9. A non-transitory computer-readable medium including one or more sequences of instructions that, when executed by one or more processors, causes:
   detecting, by a computing device, user activities during a first period of time, the detecting comprising:
   receiving device state information from a secondary device through a network interface device of the computing device; and
   identifying the user activities based on the received device state information;
   obtaining, by the computing device, sleep ritual activity information corresponding to the user, the sleep ritual activity information identifying a plurality of historical sleep ritual activities that the user historically performs before sleeping;
   comparing, by the computing device, the detected user activities to the historical sleep ritual activities to produce a comparison;
   determining, by the computing device, that the user intends to sleep at a current time based on the comparison;
   in response to determining that the user intends to sleep at the current time, identifying, by the computing device, one or more particular sleep ritual activities of the historical sleep ritual activities that the user has failed to perform within the first period of time based on the comparison; and
   causing, by the computing device, a reminder notification to be presented on a display of the computing device that identifies the one or more particular sleep ritual activities the user failed to perform.

10. The non-transitory computer-readable medium of claim 9, wherein the historical sleep ritual activities include use of the secondary device, and wherein the reminder notification reminds the user to use the secondary device to change a device state of the secondary device prior to sleeping.

11. The non-transitory computer-readable medium of claim 9, wherein the historical sleep ritual activities include a personal hygiene activity, and wherein the reminder notification reminds the user to perform the personal hygiene activity prior to sleeping.

12. The non-transitory computer-readable medium of claim 9, wherein the historical sleep ritual activities include a personal security activity, and wherein the reminder notification reminds the user to perform the personal security activity prior to sleeping.

13. The non-transitory computer-readable medium of claim 9, wherein the historical sleep ritual activities include an energy conservation activity, and wherein the reminder notification reminds the user to perform the energy conservation activity prior to sleeping.

14. The non-transitory computer-readable medium of claim 9, wherein the instructions that cause detecting the user activities include instructions that cause:
receiving sensor data from one or more sensor devices of the computing device; and
identifying the user activities based on the received sensor data.

15. The non-transitory computer-readable medium of claim 9, wherein the instructions that cause detecting the user activities include instructions that cause:
obtaining a plurality of motion samples and storing at least some of the plurality of motion samples to a motion database, each motion sample being mapped to a corresponding activity;
detecting motion of the computing device using one or more motion sensors of the computing device; and
identifying the user activities based on a comparison of the detected motion to motion samples stored to the motion database.

16. The non-transitory computer-readable medium of claim 9, wherein the identified historical sleep ritual activities include the user setting a secondary device to a particular state, and wherein the reminder notification reminds the user to change a current state of the secondary device to the particular state prior to sleeping.

17. A computing device comprising:
one or more processors; and
a non-transitory computer-readable medium including one or more sequences of instructions that, when executed by one or more processors, causes:
detecting, by the computing device, user activities during a first period of time, the detecting comprising:
receiving device state information from a secondary device through a network interface device of the computing device; and
identifying the user activities based on the received device state information;
obtaining, by the computing device, sleep ritual activity information corresponding to the user, the sleep ritual activity information identifying a plurality of historical sleep ritual activities that the user historically performs before sleeping;
comparing, by the computing device, the detected user activities to the historical sleep ritual activities to produce a comparison;
determining, by the computing device, that the user intends to sleep at a current time based on the comparison;
in response to determining that the user intends to sleep at the current time, identifying, by the computing device, one or more particular sleep ritual activities of the historical sleep ritual activities that the user has failed to perform within the first period of time based on the comparison; and
causing, by the computing device, a reminder notification to be presented on a display of the computing device that identifies the one or more particular sleep ritual activities the user failed to perform.

18. The computing device of claim 17, wherein the historical sleep ritual activities include use of the secondary device, and wherein the reminder notification reminds the user to use the secondary device to change a device state of the secondary device prior to sleeping.

19. The computing device of claim 17, wherein the historical sleep ritual activities include a personal hygiene activity, and wherein the reminder notification reminds the user to perform the personal hygiene activity prior to sleeping.

20. The computing device of claim 17, wherein the identified historical sleep ritual activities include the user setting a secondary device to a particular state, and wherein the reminder notification reminds the user to change a current state of the secondary device to the particular state prior to sleeping.

21. The computing device of claim 17, wherein the historical sleep ritual activities include a personal security activity, and wherein the reminder notification reminds the user to perform the personal security activity prior to sleeping.

22. The computing device of claim 17, wherein the historical sleep ritual activities include an energy conservation activity, and wherein the reminder notification reminds the user to perform the energy conservation activity prior to sleeping.

23. The computing device of claim 17, wherein the instructions that cause detecting the user activities include instructions that cause:
receiving sensor data from one or more sensor devices of the computing device; and
identifying the user activities based on the received sensor data.

24. The computing device of claim 17, wherein the instructions that cause detecting the user activities include instructions that cause:
obtaining a plurality of motion samples and storing at least some of the plurality of motion samples to a motion database, each motion sample being mapped to a corresponding activity;
detecting motion of the computing device using one or more motion sensors of the computing device; and
identifying the user activities based on a comparison of the detected motion to motion samples stored to the motion database.

* * * * *